July 30, 1957 E. S. BOERNER Plant Pat. 1,624
ROSE PLANT
Filed Nov. 21, 1956
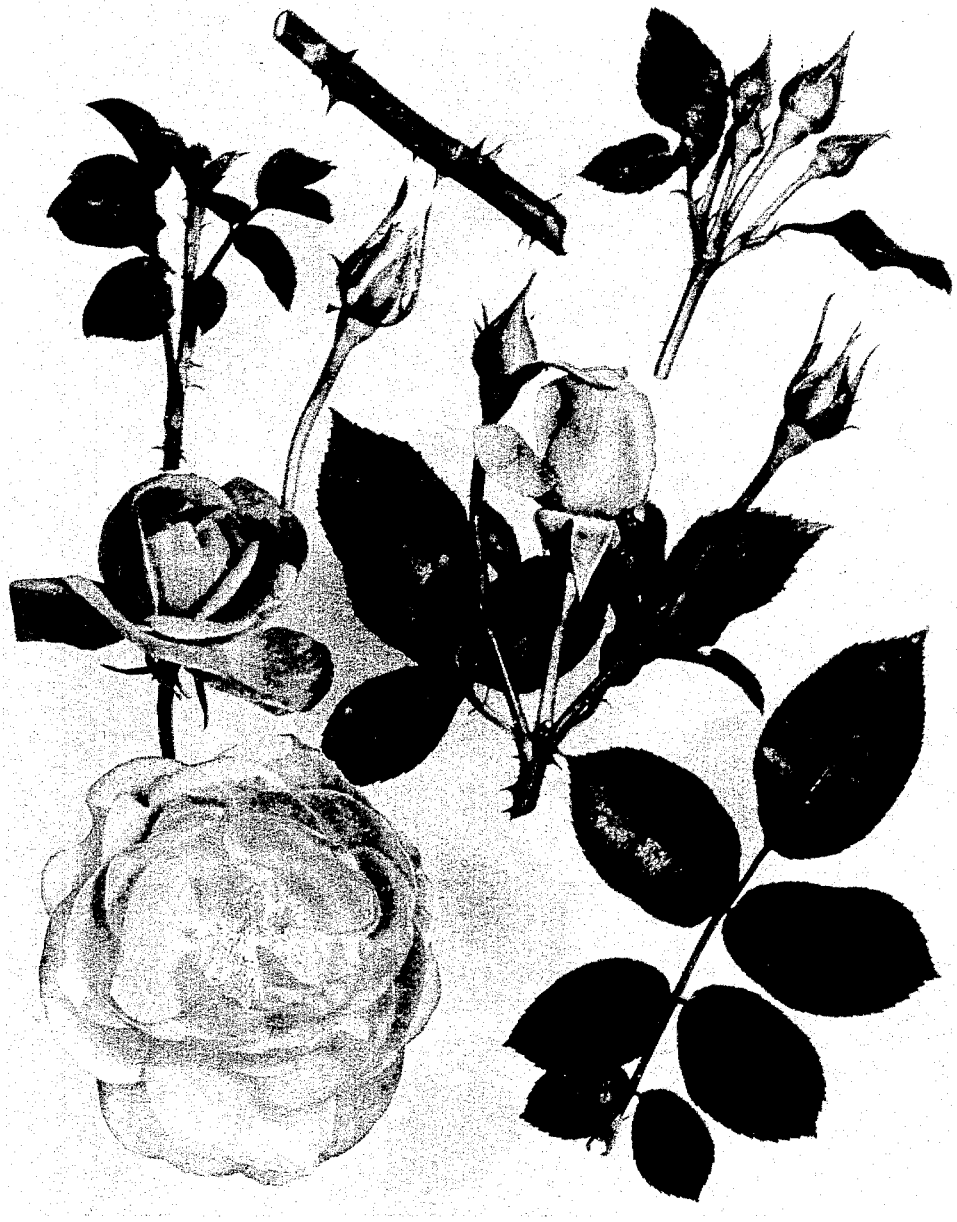
INVENTOR
E. S. Boerner
BY Robert Cobb
ATTORNEYS United States Patent Office Plant Pat. 1,624
Patented July 30, 1957

1,624

ROSE PLANT

Eugene S. Boerner, Newark, N. Y., assignor, by mesne assignments, to C. W. Stuart & Co., Newark, N. Y., a corporation of New York Application November 21, 1956, Serial No. 623,721

1 Claim. (Cl. 47—61)

The present invention relates to a new and distinct variety of rose plant of the hybrid polyantha class, which was originated by me by crossing the variety "Geranium Red" (Plant Patent No. 811) with the variety "Fashion" (Plant Patent No. 789).

As a result of this breeding, I have produced a new rose variety which is particularly characterized as to novelty by the following unique combination of outstanding features:

(1) A vigorous habit of growth;

(2) Luxurious, dark green, leathery foliage which is resistant to blackspot;

(3) Contrasting new foliage of maroon color;

(4) Very thorny branches bearing bright red thorns;

(5) Large, very free-flowering trusses;

(6) A new and distinctive flower color, the petals of which are orange-red in general color tonality, with red color on the reverse surface of the petals; and (7) Extremely fragrant flowers corresponding to that of the variety "Crimson Glory" (Plant Patent No. 105) which is one of the parents of "Geranium Red."

The foregoing characteristics definitely distinguish my new variety from its parents, as well as from all others of its class of which I am aware, and asexual reproduction thereof by budding, as performed at Newark, New York, shows that these characteristics and distinctions come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Horticultural Color Chart issued by the British Color Council in collaboration with the Royal Horticultural Society, except where general color terms of ordinary dictionary significance are obvious:

Type: Hardy; bush; outdoor; seedling; for garden decoration.

Class: Hybrid polyantha (floribunda).

Breeding: Seedling.

*Seed parent.*—"Geranium Red."

*Pollen parent.*—"Fashion."

Propagation: Holds its distinguishing characteristics through succeeding propagations by budding.

*Flower*

Locality where grown and observed: Newark, New York.

Flowers borne: Several to stem; in regular pyramidal clusters; on strong stems of medium length.

Quantity of bloom: Abundant, outdoors.

Continuity: Continuous.

Fragrance: Strong (similar to that of "Crimson Glory").

Bud:

*Peduncle.*—Form—medium to long; erect; smooth; with numerous red prickles. Color—medium reddish.

*Before calyx breaks.*—Size—medium. Form—globular; with a conspicuous neck; with foliaceous appendages on the surface of the bud; with slender foliaceous parts extending beyond the tip of the bud equal to ½ or more of its length. Color—Lettuce Green, Plate 861, page 176, overlaid with Garnet Brown, Plate 00918, page 192.

*As calyx breaks.*—Color—Chrysanthemum Crimson, Plate 824, page 179 (very dark—almost black).

*As first petal opens.*—Size—medium. Form—ovoid. Color: outside—Chrysanthemum Crimson, Plate 824, page 169; inside—Blood Red, Plate 820, page 166.

*Opening.*—Opens up well.

Bloom:

*Size (when fully open).*—Large; from 3 to 3½ inches.

*Petalage.*—Double; from 17 to 19 petals.

*Form.*—Globular at first, but becoming open-cupped; petals being at first loosely cupped and rolled inward, but later becoming loosely cupped and rolled outward at maturity.

Petals:

*Texture.*—Thick; leathery. Inside—velvety. Outside—satiny.

*Shape.*—Outside—round, with one notch. Intermediate—round, with one notch. Inside—scalloped irregularly with deformed notches.

This description of a newly opened flower was made from a rose grown outdoors in the month of September at Newark, New York:

*Color.*—Outer petal: outside surface—Rose Red, Plate 724, page 158; inside surface—Geranium Lake, Plate 20, page 20. Intermediate petal: outside surface—Rose Red, Plate 724, page 158; inside surface—Geranium Lake, Plate 20, page 20. Inner petal: outside surface—Rose Red, Plate 724, page 158; inside surface—Geranium Lake, Plate 20, page 20.

This description was made from a rose that was open for 5 days outdoors in the month of September at Newark, N. Y.:

*Color.*—Outer petal: outside surface—Rose Red, Plate 724, page 158; inside surface—Geranium Lake, Plate 20, page 20. Inner petal: outside surface—Rose Red, Plate 724, page 158; inside surface—Geranium Lake, Plate 20, page 20.

*General color effect.*—Newly opened flower—Geranium Lake, Plate 20, page 20. 3-days open—Geranium Lake, Plate 20, page 20.

*Behavior.*—Does not fade; drops off cleanly; slight tendency to burn in hot weather.

*Flower longevity.*—On bush in garden—5 days in September. Cut roses grown outdoors and kept at livingroom temperatures—4 days in September.

*Reproductive organs*

Stamens: Many; arranged regularly about pistils.

Filaments: Medium length; most with anthers. Color—Carmine, Plate 21/2, page 21.

Anthers: Large; all open at once. Color—Orange-Buff, Plate 507, page 133.

Pollen: Moderate. Color—gold.

Pistils: Many.

Styles: Even; medium length; medium heavy; columnar.

Stigma: Color—white.

Ovaries: All enclosed in calyx.

Hips: Globular; with inconspicuous neck; moderately smooth; prickly; walls thick and fleshy. Color—green-gray.

Sepals: Permanent; moderately long; spear-shaped; recurved. Color—Sage Green, Plate 000861/2, page 198, suffused with Spirea Red, Plate 025, page 112.

Seeds: Many; medium size.

*Plant*

Foliage:

*Leaves.*—Compound of 5 leaflets; very abundant; medium size; leathery; glossy.

*Leaflets.*—Shape—Oval, with apex acute. Base—round. Margin—doubly serrate.

*Color.*—Mature: upper surface—Parsley Green, Plate 00962, page 193; under surface—Sage Green, Plate 000861, page 198. Young: upper surface—Maroon, Plate 1030, page 185; under surface—Maroon, Plate 1030/2, page 185.

*Rachis (supporting stem of the compound leaf).*—Medium caliper. Upper side—prickly. Under side—extremely prickly.

*Stipules.*—Medium length; with medium length points turning out at an angle of 45°.

*Disease resistance.*—Resistant to blackspot, as determined by comparison with other varieties grown under comparable cultural conditions at Newark, N. Y.

Growth:

*Habit.*—Bushy; upright; much-branched.

*Growth.*—Vigorous.

*Canes.*—Heavy.

*Main stems.*—Color—dull green-bronze. Thorns—many; long; hooked downward; with narrow base. Prickles—many; color—red. Hairs—few; color—red.

*Branches.*—Color—dull green-bronze. Thorns—many; long; hooked downward; with narrow base. Prickles—many; color—reddish. Hairs—few; color—reddish.

*New shoots.*—Color—red. Thorns—many; long; with narrow base. Prickles—many; color—reddish. Hairs—few; color—reddish.

I claim:

A new and distinct variety of rose plant of the hybrid polyantha class, substantially as herein shown and described, characterized particularly as to novelty by its vigorous habit of growth, its luxurious, dark green, leathery foliage which is resistant to blackspot, its contrasting new foliage of maroon color, its very thorny branches and the bright red color of the thorns, its large, very free-flowering trusses, the distinctive orange-red general color tonality of its flowers having red colored surfaces on the reverse side of the flower petals, and the strong fragrance of its flowers.

No references cited.